US006818408B2

(12) United States Patent
Fukui et al.

(10) Patent No.: US 6,818,408 B2
(45) Date of Patent: Nov. 16, 2004

(54) MONOCLONAL ANTIBODY RECOGNIZING PHOSPHATIDYLINOSITOL-3,4,5-TRIPHOSPHATE

(75) Inventors: Yasuhisa Fukui, 5-7-6 Kichijouji Kita-cho, Musashino-shi, Tokyo 180-0001 (JP); Satoshi Nagata, Tokyo (JP); Ryuichi Shirai, Yokohama (JP)

(73) Assignees: Medical & Biological Laboratories Co., Ltd., Aichi (JP); Yasuhisa Fukui, Tokyo (JP)

( * ) Notice: Subject to any disclaimer, the term of this patent is extended or adjusted under 35 U.S.C. 154(b) by 0 days.

(21) Appl. No.: 10/007,790

(22) Filed: Nov. 13, 2001

(65) Prior Publication Data

US 2002/0120107 A1 Aug. 29, 2002

Related U.S. Application Data

(62) Division of application No. 09/257,069, filed on Feb. 24, 1999, now Pat. No. 6,348,580.

(30) Foreign Application Priority Data

Sep. 7, 1998 (JP) .......................................... 10-252921

(51) Int. Cl.$^7$ ........................ G01N 33/53; G01N 33/543
(52) U.S. Cl. ........................................ 435/7.1; 436/518
(58) Field of Search .......................... 435/7.1; 436/518; 530/388.1, 387.1

(56) References Cited

U.S. PATENT DOCUMENTS

| 5,912,415 A | 6/1999 | Olszewski et al. .......... 800/298 |
| 6,107,021 A | 8/2000 | Wang et al. .................... 435/5 |

FOREIGN PATENT DOCUMENTS

| WO | WO 95/20607 | 8/1995 |
| WO | WO 96/36361 | 11/1996 |

OTHER PUBLICATIONS

Glossary of biochemistry and Molecular Biology. Revised Edition. Glick DM, Portland Press, London, 1997, p. 9.*
Rameh, Lucia E., et al., "The Role of Phosphoinositide 3–Kinase Lipid Products in Cell Function"; The Journal of Biological Chemistry; 247, (13), 8347–8350, 1999.
Leevers, Sally J., et al., "Signalling through phosphoinositide 3–kinases: the lipids take center stage".
Fukui, Yasuhisa, et al., "Downstream of Phosphatidylinositol–3 Kinase, a Multifunctional Signaling Molecule, and Its Regulation in Cell Responses"; J. Biochem. 124, (1–7), 1998.
Van der Kaay, Jeroen, et al., "A Novel, Rapid, and Highly Sensitive Mass Assay for Phosphatidylinositol 3,4,5–Triphosphate (PtdIns(3,4,5)P$_3$)P$_3$ Production in Rat Skeletal Muscle in Vivo"; The Journal of Biological Chemistry; 272 (9), 5477–5481, 1997.

Lu, Pei–Jung, et al., "Selective Recognition of Phosphatidylinositol 3,4,5–Trisphosphate by a Synthetic Peptide"; The Journal of Biological Chemistry; 272 (1), 446–472, 1997.
Miyazawa, Atsuo, et al., "Production and Characterization of Monoclonal Antibodies that Bind to Phosphatidylinositol 4,5–Bisphosphate"; Molecular Immunology; 25, (10), 1025–1031, 1988.
Fry, Michael J., "Structure, regulation and function of phosphoinositide 3–kinases"; Biochimica at Biophysica Acta 1226, 237–268, 1994.
Serunian, Leslie A., et al., "[8] Identification and Quantification of Polyphosphoinositides Produced in Response to Platelet–Derived Growth Factor Stimulation"; Methods in Enzymology; 198, 78–87, 1991.
Tolias, Kimberly F., et al., Pathways for phosphoinositide synthesis; Chemistry and Physics of Lipids; 98, 69–77, 1999.
Thomas, C.L., et al., "Generation of phosphatidylinositol–specific antibodies and their characterization"; Biochemical Society Transactions; 27 (4), 648–652, 1999.
Sawada, Takayuki, et al., "Synthesis of 1–O–Alkyl– and 1–O–Acyl–myo–inositol 3,4,5–trisphosphates as Novel Analogues of Phosphatidyl–myo–inositol 3,4,5–trisphosphate"; Bioorganic & Medicinal Chemistry Letters; 5 (19), 2263–2266, 1995.
Clarkson, Tim, et al., "Making antibody fragments using phage display libraries", Nature, vol. 352, 624–628, 1991.
Appella, Ettore, et al., "Amino Acid Sequence of the Variable Region of M149 Mouse Myeloma Light Chain: Comparison with the Nucleotide Sequence of K2 and K3 Clones"; Molecular Immunology; 17, 1507–1513, 1980.
Morita, et al, Tennen Yuki Kagobutsu Toronkai Yoshisyu 39$^{th}$; 43–48, 1997.
Ettore Appella and Vernon L. Alvarez, "Amino Acid Sequence Of The Variable Region Of M149 Mouse Myeloma Light Chain: Comparison With The Nucleotide Sequence of K2 and K3 Clones"; *Molecular Immunology*, vol. 17, pp. 1507–1513, 1980.
Fry, Michael J., "Structure regulation and function of phosphoinositide 3–kinases", Biochimica at Biophysica Acta 1225, 237–268, 1994.

* cited by examiner

*Primary Examiner*—S. Devi
(74) *Attorney, Agent, or Firm*—David G. Conlin; Christine C. O'Day; Edwards & Angell, LLP

(57) ABSTRACT

A novel monoclonal antibody that specifically recognizes phosphatidylinositol-3,4,5-triphosphate (PIP3) but does not cross-react with structurally similar phospholipid antigens is advantageous for PIP3-specific immunoassay. The gene in the variable regions of the monoclonal antibody has been identified, which enables producing recombinant antibodies.

4 Claims, 8 Drawing Sheets

Fig.5
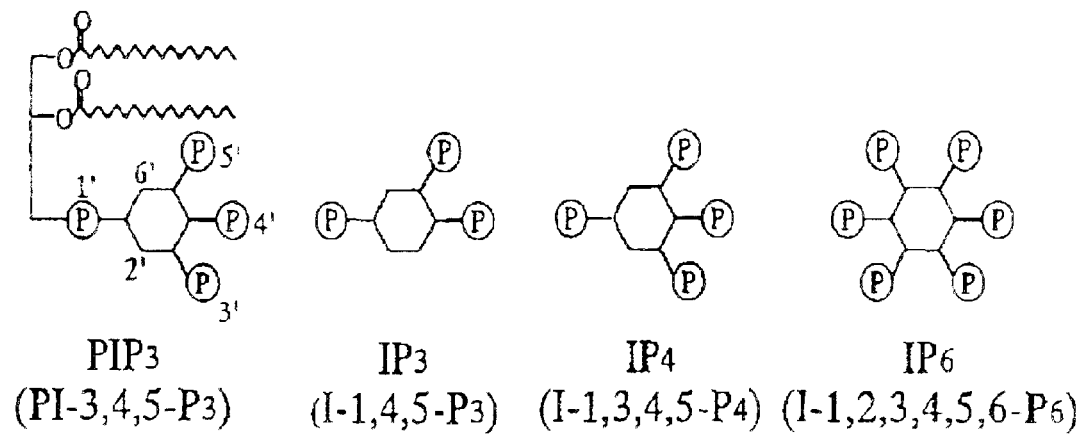
PIP3　　　　　IP3　　　　　IP4　　　　　IP6
(PI-3,4,5-P3)　(I-1,4,5-P3)　(I-1,3,4,5-P4)　(I-1,2,3,4,5,6-P6)
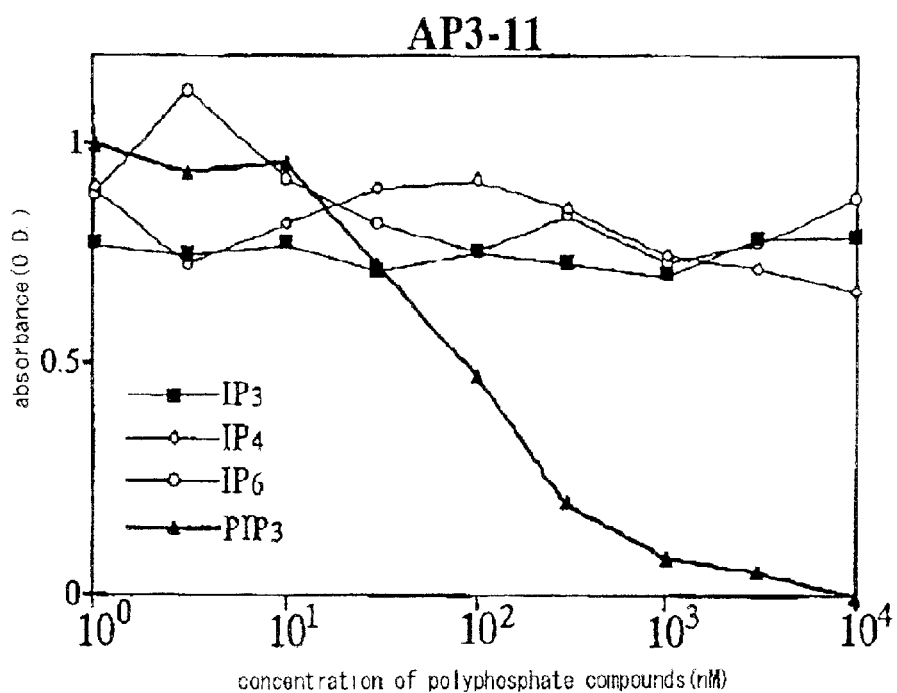

Amino acid Sequence of AP3-11 variable regions

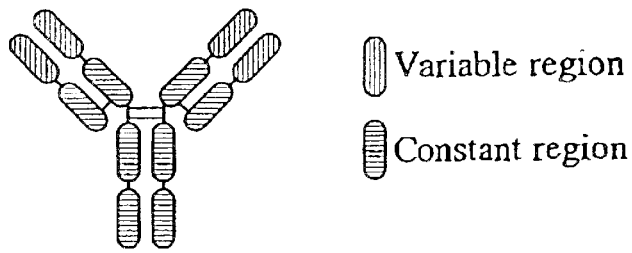

- Variable region
- Constant region

Light Chain Variable Region (SEQ ID NO:4)

DIQMTQSPASLSASVGETVTITC[RASENIYSYLP]WYQQ (CDR L1, SEQ ID NO:8)

NQGKSPQLLVY[NAKTLIE]GVPSRFSGSGSGTQFSLKIN (CDR L2, SEQ ID NO:9)

SLQPEDFGSYYC[QHHYGTPYT]FGGGTKLEIK (CDR L3, SEQ ID NO:10)

Heavy Chain Variable Region (SEQ ID NO:2)

EVQLQQSGPEVVKTGASVKISCKAS[GYSFTGY]YMHWV (CDR H1, SEQ ID NO:5)

KQSHGKSLEWIGYI[SCYNA]ATRYNQKFKGKATFTVDTS (CDR H2, SEQ ID NO:6)

SSTAYMQFNSLTSEDSAVYYCAR[SGAYYRYGVVY]WGQ (CDR H3, SEQ ID NO:7)

GTLVTVSAATTT

FIG. 8

MONOCLONAL ANTIBODY RECOGNIZING PHOSPHATIDYLINOSITOL-3,4,5-TRIPHOSPHATE

The present application is a Divisional Application of U.S. Ser. No. 09/257,069, filed Feb. 24, 1999, which issued as U.S. Pat. No. 6,348,580 on Feb. 19, 2002, which in turn claimed the priority benefit of Japanese Patent Application No. 10-252921, filed Sep. 7, 1998.

FIELD OF THE INVENTION

The present invention relates to a monoclonal antibody to phosphatidylinositol-3,4,5-triphosphate. The present invention also relates to a method for immunoassay of phosphatidylinositol-3,4,5-triphosphate using the monoclonal antibody.

BACKGROUND OF THE INVENTION

The basic system for survival of multicellular organisms, including humans, includes a "cellular signal transduction system," in which an extracellular signal is transferred to the inside of the cell to induce a necessary cell response. It is becoming clear that abnormality in this system causes pathological conditions attributed to an inadequate cell response, such as neoplastic transformation of cells. Phosphatidylinositol (hereinafter abbreviated as PI), which is a phospholipid present in various biomembranes, changes the phosphorylated state of the inositol ring by the action of enzymes activated by extracellular stimulation to transduce an extracellular signal into cells. Phosphatidylinositol-3,4,5-triphosphate with a phosphorylated inositol group at the 3-position has been shown, inter alia, to be produced from phosphatidylinositol-4,5-biphosphate (hereinafter abbreviated as PI-4,5-P2) by the action of phosphatidylinositol-4,5-kinase (hereinafter abbreviated as PI3K) activated by stimulating various proliferation or differentiation factors and to participate not only in signal transduction into the cell nucleus but also in versatile and fundamental cell responses such as construction of cell backbone and vesicular transport of substances (Fukui, Y. et al., J. Biochem., 124, 1–7, 1998). Phosphatidylinositol-3,4,5-triphosphate used herein is abbreviated PIP3; if it is necessary to specify the phosphorylated position, the triphosphate is designated PI-3,4,5-P3. The structure of PIP3 is schematically shown below.

PIP3

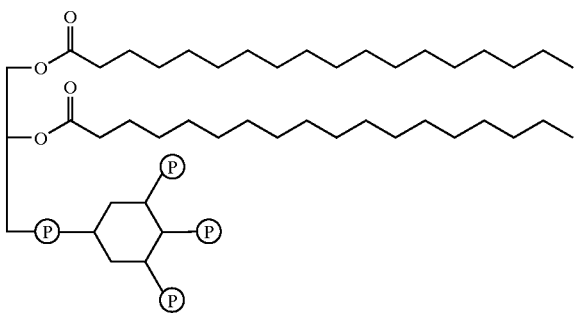

Studies on the kinetics of PIP3 both in cells and in living organisms help clarify the fundamental cellular signal transduction and shed light on pathological conditions of various diseases. The role of PIP3 in cells has been explored so far mainly by indirect means of using PI3K inhibitors or modifiers such as activated or inactivated PI3K. As a direct approach, a quantitative assay has been established for PIP3.

However, the known assay for PIP3 requires using a radioisotope, which necessitates special facilities for the assay. Moreover, the assay itself is time-consuming due to complicated operations including extraction and chromatography in many steps. Therefore, a simple assay technique has been desired.

For instance, antibodies that can recognize PIP3 will be important tools for further investigations. These antibodies will be useful for purification and immunoassay of PIP3 or as inhibitors against PIP3. However, phospholipid antigens are generally known to have a poor antigenicity. It is thus difficult to obtain antibodies to the antigens. PIP3 has an additional problem in that it is difficult to produce in large quantities. Though attempts to produce the antibodies using elaborated adjuvants were reportedly successful, most of the antibodies produced have a poor ability to recognize the phosphorylated state of PI. In most cases, it is difficult to distinguish PIP3 from PI or PI-4,5-P2 due to their cross-reactivity.

It has been reported that a rabbit was immunized to produce a polyclonal antibody to PI-4,5-P2 (Molec. Immun., 16, 193–196, 1979). The polyclonal antibody exhibited cross-reactivity with other phospholipid antigens such as phosphatidylinositol-4-phosphate (hereinafter abbreviated as PI-4-P) or cardiolipin (hereinafter abbreviated as CL). A monoclonal antibody to PI-4-P was obtained by immunization with liposomes (Molec. Immun., 21, 863–868, 1984). However, it was confirmed that the antibody was also cross-reactive with other phospholipids, that is, the cross-reactivity with PI-4,5-P2 was observed by the complement-dependent liposome lysis assay.

A monoclonal antibody to PI-4,5-P2 was produced using as an immunogen a suspension of PI-4,5-P2 together with phosphatidylcholine or methylated BSA (Proc. Japan Acad., 59, 28–32, 1983). The thus-produced monoclonal antibody has been verified to be cross-reactive with an acidic phospholipid such as PI-4-P or PI. Furthermore, a monoclonal antibody specific to PI-4,5-P2 and showing a low cross-reactivity with other phospholipids was obtained using a Salmonella cell as an adjuvant (Miyazawa A., Molec. Immun., 26, 1025–1031, 1988). However, there has been no report of an antibody highly specific to PIP3 and non-cross-reactive with other phospholipid antigens being obtained. For this reason, no immunoassay technique for PIP3 has been found yet. Immunoassay is an excellent technique that can achieve a high sensitivity and accuracy in a simple operation. Accordingly, an immunological assay for PIP3 is strongly desired for further studies on cellular signal transduction.

SUMMARY OF THE INVENTION

An objective of the present invention is to provide an antibody specifically recognizing PIP3. Another objective of this invention is to provide an immunological assay method using the antibody. More specifically, the present invention seeks to provide a novel antibody specifically recognizing PIP3 and a simple method for determining PIP3 with high sensitivity, like enzyme immunoassay, without requiring any special facilities.

Producing an anti-PIP3 antibody is a problem because it is difficult to obtain a large quantity of antigens and the poor antigenicity of phospholipids used as antigens makes it difficult to produce an antibody of high titer. The inventors have solved the former problem by chemical synthesis of PIP3 that enables it to be produced in large quantities. The inventors have also overcome the problem of poor antigenicity by enhancing the antigenicity, using an immunogen obtained through adsorption of PIP3 to dead Salmonella cells. In this way, the inventors have succeeded in producing a novel monoclonal antibody that binds specifically to PIP3. Using the antibody, an immunological assay specific to PIP3 in the living organism can be performed successfully. Furthermore, the inventors have isolated a gene encoding the amino acid sequence that constitutes variable regions of the antibody and have determined the nucleotide sequence, which will enable producing recombinant antibodies. The inventors have also found that topological PIP3 distribution in cells can be identified and inhibitors specific to the function of PIP3 can be developed, using the antibody of the present invention.

Specifically, the present invention relates to the following antibody and variable regions thereof as well as an immunological assay method using the antibody.

(1) An antibody specifically recognizing phosphatidylinositol-3,4,5-triphosphate.

(2) An antibody of (1), wherein the antibody is a monoclonal antibody.

(3) An antibody of (2), which recognizes an antigenic determinant comprising an inositol group and a glycerol backbone in phosphatidylinositol-3,4,5-triphosphate.

(4) An antibody of any one of (1) through (3), which is non-cross-reactive with phosphatidylinositol-4,5-diphosphate.

(5) A variable region of immunoglobulin heavy chain specifically binding to phosphatidylinositol-3,4,5-triphosphate, comprising an amino acid sequence shown by SEQ ID NO: 2 or an amino acid sequence of SEQ ID NO: 2 in which one or more amino acid residues have been substituted, deleted or added.

(6) A variable region of immunoglobulin light chain specifically binding to phosphatidylinositol-3,4,5-triphosphate, comprising an amino acid sequence shown by SEQ ID NO: 4 or an amino acid sequence of SEQ ID NO: 4 in which one or more amino acid residues have been substituted, deleted or added.

(7) CDR1 in immunoglobulin heavy chains specifically binding to phosphatidylinositol-3,4,5-triphosphate, comprising an amino acid sequence shown by SEQ ID NO: 5 or an amino acid sequence of SEQ ID NO: 5 in which one or more amino acid residues have been substituted, deleted or added.

(8) CDR2 in immunoglobulin heavy chains specifically binding to phosphatidylinositol-3,4,5-triphosphate, comprising an amino acid sequence shown by SEQ ID NO: 6 or an amino acid sequence of SEQ ID NO: 6 in which one or more amino acid residues have been substituted, deleted or added.

(9) CDR3 in immunoglobulin heavy chains specifically binding to phosphatidylinositol-3,4,5-triphosphate, comprising an amino acid sequence shown by SEQ ID NO: 7 or an amino acid sequence of SEQ ID NO: 7 in which one or more amino acid residues have been substituted, deleted or added.

(10) CDR1 in immunoglobulin light chains specifically binding to phosphatidylinositol-3,4,5-triphosphate, comprising an amino acid sequence shown by SEQ ID NO: 8 or an amino acid sequence of SEQ ID NO: 8 in which one or more amino acid residues have been substituted, deleted or added.

(11) CDR2 in immunoglobulin light chains specifically binding to phosphatidylinositol-3,4,5-triphosphate, comprising an amino acid sequence shown by SEQ ID NO: 9 or an amino acid sequence of SEQ ID NO: 9 in which one or more amino acid residues have been substituted, deleted or added.

(12) CDR3 in immunoglobulin light chains specifically binding to phosphatidylinositol-3,4,5-triphosphate, comprising an amino acid sequence shown by SEQ ID NO: 10 or an amino acid sequence of SEQ ID NO: 10 in which one or more amino acid residues have been substituted, deleted or added.

(13) An immunogen composition for use in producing an antibody of any one of (1) through (4), comprising a mixture of a dead Salmonella cell as an adjuvant and phosphatidylinositol-3,4,5-triphosphate.

(14) A method for producing an antibody of any one of (1) through (4), which comprises immunizing an immunogen composition of (13).

(15) An immunoassay method which comprises the steps of reacting the antibody of any one of (1) through (4) or a variable region thereof with phosphatidylinositol-3,4,5-triphosphate present in a sample, and detecting the binding based on an immunological reaction between the antibody or a variable region thereof and the triphosphate.

(16) An immunoassay method of (15), which comprises observing the degree to which the immunological reaction between the antibody or a variable region thereof and an antigenic determinant recognized thereby is inhibited by phosphatidylinositol-3,4,5-triphosphate present in a sample.

(17) A kit for immunoassay for phosphatidylinositol-3,4,5-triphosphate comprising the antibody of any one of (1) through (4) or a variable region thereof.

BRIEF DESCRIPTION OF THE DRAWINGS

FIG. 5 shows graphs showing the results of indirect ELISA performed to verify the cross-reactivity of AP3-11 with various inositol polyphosphates. The ordinate designates absorbance, and the abscissa designates the concentration (nM) of polyphosphate compounds which are competitive compounds.

FIG. 8 schematically shows a predicted hyper variable region (complementarity determining region (CDR)) in the variable region in each of the light chains and the heavy chains of the antibody AP3-11.

DETAILED DESCRIPTION OF THE INVENTION

Figure 1:
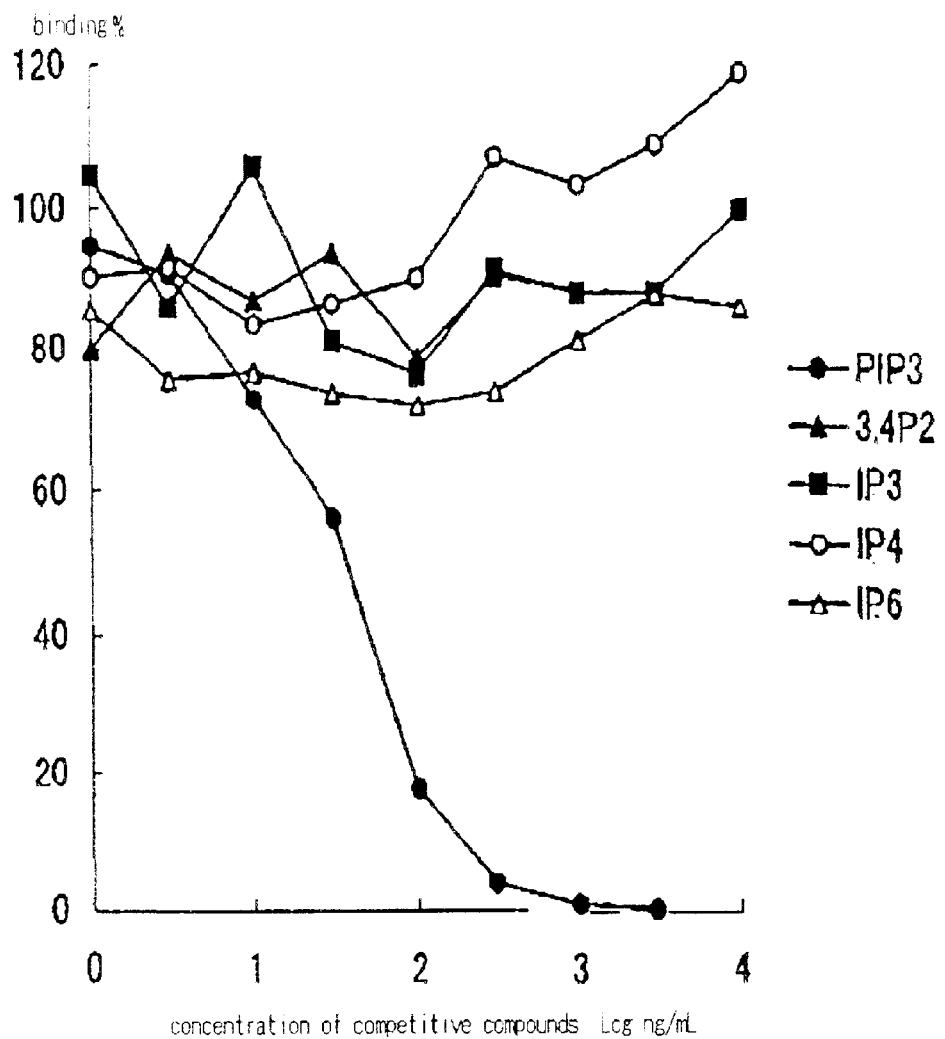
FIG. 1 shows graphs showing the results of indirect enzyme-linked immunosorbent assay (hereinafter referred to as ELISA) performed to verify the cross-reactivity of AP3-11 with various inositol polyphosphates. The ordinate designates the binding (%) of the antibody AP3-11, and the abscissa designates the concentration (Log ng/mL) of competitive compounds.

The antibody of the present invention specifically recognizes PIP3 but is not cross-reactive with PI-4,5-P2. Throughout the specification, the term "specific to PIP3" means that the antibody can recognize the phosphorylated state of PIP3 and immunologically distinguish PIP3 from other phosphorylated compounds. The antibody of the present invention can be produced by the following immunological procedures. PIP3 is suspended together with the killed Salmonella cells, and the resulting suspension is used as an immunogen. In more detail, lipopolysaccharides are removed from the dead Salmonella cells (Galanos C., Eur. J. Biochem., 24, 116–122, 1971). PIP3 is then coated onto the dead cells to prepare a suspension for use as an immunogen (Umeda M., J. Immun., 137, 3264–3269, 1986). PIP3 may be purified from cells or chemically synthesized. Chemical synthesis of PIP3 is known and described in Sawada T., Bioorganic & Medicinal Chemistry Letters, 5, 2263–2266, 1995. An animal suitable for immunization is immunized with PIP3. When an increase in the antibody titer is confirmed, the antibody is recovered. The antibody may be polyclonal or monoclonal. The monoclonal antibody is more advantageous in that an antibody with a higher specificity can be selected. Furthermore, when the monoclonal antibody is established, it enables cloning cDNA coding for the amino acid sequences that constructs the variable regions of the monoclonal antibody having a desired binding activity, as will be described later.

The monoclonal antibody can be produced by cloning antibody-producing cells. In general, antibody-producing cells recovered from the immunized animal are subjected to cell fusion with an appropriate fusion partner. The resulting hybridomas are then screened in terms of the activity of the produced antibodies (Gulfre G., Nature, 266, 550–552, 1977). When mice are employed as the animal for immunization, mouse-derived myeloma cells such as P3-X63-Ag.653 are adequate as the fusion partner. The hybridomas subjected to HAT selection are screened first in terms of the binding activity to PIP3. The hybridomas producing the antibodies that have the binding activity to PIP3 are then subjected to a cross-reactivity test. In this test, the binding activity to other phospholipid antigens is examined to screen hybridomas having an acceptable cross-reactivity. Acceptable cross-reactivity means a cross-reactivity that can be disregarded for the desired use of the antibody. When the monoclonal antibody is employed for an immunological assay, it has no substantial cross-reactivity if a signal provided by the cross-reactivity is reduced to the level of the background in the final assay system.

ELISA or liposome lysis assay is useful for verifying the reactivity of PIP3 or the cross-reactivity with other phospholipid antigens. In ELISA, microtiter plates sensitized with an antigen whose reactivity is to be observed are prepared. A sample solution obtained by suitably diluting the hybridoma supernatants is then added to the wells of the microtiter plates to initiate a reaction. After a thorough reaction, the wells are washed, and a second antibody to immunoglobulin is then added for further reaction. The second antibody finally bound to each well is assayed. Thus, the binding activity of the antibody present in the culture supernatant to the antigen can be quantitatively determined. ELISA has been demonstrated for an antibody using a phospholipid antigen (Umeda M., J. Immun., 136, 2562–2567, 1986).

The liposome lysis assay utilizes the phenomenon that when an antibody reacts with an antigen-sensitized liposome, the liposome lyses by the action of the complement. Since the action of the complement is utilized, the technique is called complement-dependent liposome lysis assay. Liposomes comprise phospholipid antigens to be examined in addition to dicetyl phosphate (hereinafter abbreviated as DCP), dimyristoyl phosphatidylcholine (hereinafter abbreviated as DMPC), and cholesterol. These lipid components are dissolved in an appropriate organic solvent. The solution is then dried to prepare a lipid film. When the film is added to an aqueous solvent and the mixture is agitated vigorously, liposomes of multilamellar structure are formed. In the liposomes thus prepared, phospholipid antigens are taken up as membrane-constructing components. For this reason, an antigenic structure close to the antigen present in actual cell membranes is presented. It is thus appropriate for screening the monoclonal antibody. For easy screening, a fluorescent dye can be enclosed in the liposomes as a lysis marker. Typical examples of the fluorescent dye include 4-methylumbelliferyl phosphate and calcein. When the antibody binds to this liposome-constructing phospholipid antigen in the presence of its complement, the liposome is broken down to release the fluorescent dye in the liposome. This phenomenon is observed as increased fluorescence intensity in the liquid phase. Complement-dependent liposome lysis assay using phospholipid antigens such as PI-4,5-P2 is known (Molec. Immun., 26, 1025–1031, 1988). The phospholipids used to verify the cross-reactivity are phospholipid antigens having a similar structure. The cross-reactivity should be verified with analogous substances having a similar partial structure. Specific examples of such compounds are given below, and their structural characteristics will be shown in examples below.

| PC | phosphatidylcholine |
|---|---|
| PS | phosphatidylserine |
| PA | phosphatidic acid |
| PI | phosphatidylinositol |
| CL | cardiolipin |
| PE | phosphatidylethanolamine |
| PI-4,5-P2 | phosphatidylinositol-4,5-biphosphate |
| IP3 | 1,4,5-inositol triphosphate |
| IP4 | 1,3,4,5-inositol tetraphosphate |
| IP6 | 1,2,3,4,5,6-inositol hexaphosphate |

In both ELISA and liposome lysis assay, the cross-reactivity of the antibody with other phospholipid antigens can be verified by the reaction system using PIP3 as an antigen. That is, to the reaction system containing PIP3 and the antibody to be examined for its specificity are added other antigens to be examined for the cross-reactivity with the antibody and the competitive reaction is then observed to confirm the cross-reactivity. This technique for verifying the cross-reactivity by means of the competitive inhibition is useful for rapid screening since it is unnecessary to prepare the reaction system for all antigens.

The procedures described above can yield an antibody of the present invention that has binding activity to PIP3 and can immunologically distinguish PIP3 from structurally similar antigens such as PI-4,5-P2.

The present invention further provides the amino acid sequences constituting the variable regions of the novel antibody having a desired binding activity to PIP3 and the nucleotide sequences encoding the same. More specifically, the present invention provides the immunoglobulin variable regions containing the amino acid sequences shown by SEQ ID NO: 2 and SEQ ID NO: 4. The present invention further provides cDNA encoding the immunoglobulin variable regions containing the nucleotide sequences shown by SEQ ID NO: 1 and SEQ ID NO: 3. SEQ ID NO: 1 and SEQ ID NO: 2 are deduced from the heavy chain and, SEQ ID NO: 3 and SEQ ID NO: 4 from the light chain, in the immunoglobulin molecule. These amino acid sequences or cDNA nucleotide sequences are not necessarily identical but may vary so long as the specific binding activity to PIP3 is maintained. As will be later described, particularly the site corresponding to CDR is highly variable. In the CDR region, even amino acids may vary some occasions.

In general, each immunoglobulin molecule consists of heavy chains having a larger molecular weight and light chains having a smaller molecular weight. The heavy and light chains each carries a region called "a variable region" in about 110 amino acid residues at the N-terminus, which are different between the molecules. Variable regions of a heavy chain and a light chain are designated VH and VL, respectively. The antigen-binding site is formed by forming a dimer through electrostatic interaction between the heavy chain variable region VH and the light chain variable region VL. The variable region consists of three complementarity determining regions (CDRs) and four frameworks. The CDR forms a complementary steric structure with the antigen molecule and determines the specificity of the antibody. The three CDRs inserted between the four framework regions (FRS) are present like a mosaic in the variable region (E. A. Kobat et al., Sequences of proteins of immunological interest, vol. I, 5th edition, NIH Publication, 1991). The amino acid sequences of FRs are well conserved, but those of CDR are highly variable and may thus be called hypervariable regions. Among the amino acid sequences of the antibody specifically recognizing PIP3, a CDR that determines the binding activity to antigens has been clarified in the present invention. Thus, the present invention further provides the CDR shown below (numbering the N-terminal amino acid residue as 1 in SEQ ID NO: 1 or 3), in which the number in parentheses corresponds to the SEQ ID number.

|      | Heavy Chain | Light Chain |
| --- | --- | --- |
| CDR1 | 26–32 (5)   | 24–34 (8)   |
| CDR2 | 52–56 (6)   | 50–56 (9)   |
| CDR3 | 99–109 (7)  | 89–97 (10)  |

The cDNAs bearing the nucleotide sequences coding the variable regions in immunoglobulin molecules can be cloned from hybridomas that produce the monoclonal antibody to PIP3. More specifically, PCR is performed using the signal sequence of the gene in the variable regions and the nucleotide sequence in the constant regions. The amplified product is introduced into an appropriate cloning vector for further amplification to produce a library of variable genes. Since the site corresponding to CDR will be a sequence specific to the variable regions of the present invention, positive clones are screened from the library of the variable regions using the site as a probe. The resulting cDNA is inserted into a phage by linking the light and heavy chain variable region genes through an appropriate linker. Thus, the cDNA may be expressed as a single-stranded antibody (so-called ScFV). Alternatively, known immunoglobulins are inserted into a vector for expression to utilize the same for producing immunoglobulins. Examples of the vector for expressing immunoglobulins without limit include a SV40 virus-based vector and a BPV (papilloma virus)-based vector. For example, BCMGS Neo vector, one of the BPV vectors (Hajime Karasuyama, "Bovine Papilloma Virus Vector" from the extra issue of JIKKEN IGAKU (Experimental Medicine): IDENSHI KOGAKU (Genetic Engineering) Handbook, edited by Masami Muramatsu & Hiroto Okayama, Yodosha Publishing Co., pp. 297–299, 1991), is desirable since the vector is transformed to COS7 cells to express a foreign gene efficiently.

Alternatively, the specificity of the antibody of the present invention may also be artificially reconstructed by incorporating the CDR into the framework of an optional immunoglobulin molecule. Such a technique is called the CDR grafting antibody technique (P. T Jones et al., Nature, 321, 522, 1986) and has already been established for humanizing mouse immunoglobulins. The CDRs of the present invention include not only those completely identical but also variants so long as the specificity to PIP3 is maintained. That is, the CDR amino acid sequences in which one or more amino acid residues are modified may also be used as the CDR sequence. The modified amino acid residues in the amino acid sequences of the CDR variant are preferably 30% or less, more preferably 20% or less, most preferably 10% or less, within the entire CDR. Any FR can be used as the FR into which the CDRs are to be incorporated. The CDRs of the present invention are originally derived from mouse immunoglobulins. However, the CDRs may be inserted into FRs of not only mouse immunoglobulins but also immunoglobulins of other species. The cDNAs encoding the variable regions thus constructed may be expressed by incorporating the same into the vectors described above.

In introducing mutations into CDRs, the above-described phage vector may be employed. The phage vector can express the antibody activity rapidly and hence can rapidly screen mutants. Moreover, the phage vector expresses the antibody molecule on the surface of host bacteria in an amount sufficient for screening. A mutation introduced into the CDRs remarkably increases the antibody binding activity. Thus, a single-stranded antibody having an improved binding activity can be produced using the CDRs of the present invention.

The variable regions and CDR-incorporated variable regions provided by the present invention may be expressed in their original forms. Alternatively, these variable regions may be expressed as complete immunoglobulin molecules by linking to a gene encoding the constant regions.

To express variable regions by the cDNA-incorporated vector or by the vector bearing the insert obtained by linking CDR alone to a certain FR, a dimer of the heavy and light chains can be produced by expressing heavy chain variable regions and light chain variable regions in the same host cell. This can be done by co-transformation of a host cell with a light chain expression vector and a humanized heavy chain expression vector. The antibody of the present invention can be produced from the transformant. Preferred examples of the host for the transformation include Chinese hamster ovary (CHO) cells (A. Wright & S. L. Morrison, J. Immunol., 160, 3393–3402, 1998) and SP2/0 cells (mouse myeloma) (K. Motmans et al., Eur. J. Cancer Prev., 5, 512–519,1996; R. P. Junghans et al., Cancer Res., 50, 1495–1502, 1990). The transformation can be performed by the lipofectin method (R. W. Malone et al., Proc. Natl. Acad. Sci. USA, 86, 6077, 1989, P. L. Felgner et al., Proc. Natl. Acad. Sci. USA, 84, 7413, 1987), the electroporation method, the calcium phosphate method (F. L. Graham & A. J. van der Eb, Virology, 52, 456–467, 1973), or the DEAE-Dextran method.

When the expressed variable region is accompanied by the constant region, the expression product may be purified through a protein A column, a protein G column, an anti-immunoglobulin antibody affinity column, etc. to recover the product as a purified protein. When only the variable region is expressed, these techniques for purification do not apply. In that case, other suitable purification methods should be selected. For example, if the variable region is expressed as the product fused to a protein such as a histidine tag at the C-terminus, then the expression product is purified by affinity chromatography using the corresponding ligand.

According to the present invention, PIP3 can be immunologically assayed using the thus produced monoclonal antibody or variable regions thereof. Immunological assay of PIP3 was impossible by conventional methods since an antibody itself specific to PIP3 was not available. The antibody of the present invention provides excellent specificity to PIP3 and hence provides an ideal immunological method for assaying PIP3.

According to the present invention, PIP3 can also be assayed by observing the degree of PIP3 inhibition, utilizing the phenomenon that the binding between PIP3 and the antibody of the present invention (including the variable regions) is inhibited by PIP3 originating from a sample to be analyzed. One inhibition assay that realizes such an assay principle utilizes immobilized PIP3. In more detail, PIP3 is adsorbed onto a container like a microtiter plate. A sample solution is added to the plate. PIP3 can be physically adsorbed onto the container wall after it is dissolved in an appropriate carrier such as phosphatidylcholine. The antibody of the present invention is then added, causing a competitive reaction between PIP3 adsorbed on the container and PIP3 in the sample solution with the antibody of the present invention. The antibody bound (or unbound) to the solid phase can be readily assayed by labeling the antibody with an appropriate marker. The quantity of PIP3 present in the sample solution can then be determined by comparison with the results obtained from a standard solution. The antibody can be labeled with a marker such as an enzyme, a fluorescence or a luminiferous substance. PIP3 can be assayed in a biological sample solution such as a tissue, a cultured cell, or a body fluid like blood or serum. The foregoing competitive reaction may also be performed by immobilizing the antibody of the present invention onto the wall of a container. In this case, the labeled PIP3 is reacted with the antibody concurrently with a PIP3-containing sample.

The sample for the immunological assay may be either liquid or solid. For example, a tissue specimen is immunologically stained to observe the presence or absence of PIP3 or localization of PIP3. In a preferred embodiment, the antibody of the present invention recognizes the epitope formed by the inositol group and the glycerol backbone of PIP3. Since the epitope is assumed to be exposed on the surface of the cell membrane, the antibody is useful for staining a tissue specimen. In this case, localization of several phospholipids may be observed in the same sample by using the antibody in combination with another antibody specifically recognizing a phospholipid, e.g., PI-4,5-P2. A known double-staining technique involves staining the same sample using different antibodies each labeled with fluorescent dyes having different wavelengths.

The present invention further provides a kit for use in the immunoassay described above. More specifically, the kit of the present invention comprises the antibody of the present invention, a substrate required for detecting the label, positive control, negative control, and a buffered solution used for diluting and washing a sample.

The present invention provides a monoclonal antibody that specifically binds to PIP3. The present invention further provides an immunological assay method using the antibody. The experimental results revealed that the antibody recognizes, as the epitope, not only the inositol group but also the glycerol backbone of PIP3. Thus, the antibody of the present invention can distinguish PIP3 from other inositol compounds.

The present invention further provides the gene encoding the variable regions of the antibody and hence enables producing recombinant antibodies. Since the antibody of the present invention is highly specific to PIP3, the location of PIP3 in cells can be identified. Alternatively, signal transduction by PIP3 to the downstream can be inhibited using the specificity of the antibody to PIP3 to investigate any affect caused. The present invention facilitates conducting studies that could not be conducted by conventional assay methods.

The present invention will be described below in more detail with reference to examples. However, this invention is not to be construed to be limited to those examples.

EXAMPLE 1

Producing Anti-PIP3 Monoclonal Antibody

To produce anti-PIP3 antibody, synthesized PIP3 was coated onto dead Salmonella cells as an adjuvant. The coated cells were then used as an immunogen. Namely, Salmonella minnesota was cultured overnight to recover the cells. The cells were centrifuged and washed twice with distilled water and once with diethyl ether, then dried in vacuo. The cells were then dispersed in a 1% aqueous acetic acid solution. The dispersion was heated at 100° C. for 2 hours to remove liposaccharide-linked oligosaccharides (Galanos C., Eur. J. Biochem., 24, 116–122, 1971). The thus treated cells were washed and coated with 4 µg of PIP3. The resulting suspension was used as the immunogen (for single-use) (Umeda M., J. Immun., 137, 3264–3269, 1986). PIP3 was chemically synthesized by the known method (Sawada T., Bioorganic & Medicinal Chemistry Letters, 5, 2263–2266, 1995). The immunogen was injected into Balb/c mice via the tail veins a few times every other week. In the mice with an increased antibody titer, the spleen cells were fused with myeloma cells P3-X63-Ag.653 to produce hybridomas.

Following the HAT selection, hybridoma supernatants were screened for the antibodies in terms of the binding activity to PIP3. The binding activity of the antibodies was screened by liposome lysis assay. At the same time, the antibodies that produced positive clones were tested for the cross-reactivity by indirect ELISA.

In the liposome lysis assay, PIP3 (1%), phosphatidylcholine (40%), cholesterol (40%) and dicetyl phosphate (9%) were dissolved in chloroform and distilled to dryness under reduced pressure to prepare a lipid film. After a highly concentrated aqueous solution of calcein (fluorescent dye) was added to the film, the mixture was vigorously stirred to prepare calcein marker-enclosed multilamellar liposomes. The culture supernatant was added to the liposomes together with the complement so that the antigen-antibody binding occurred to activate the complement and break the membrane. When the antibody bound to PIP3 is present in the culture supernatant, the highly concentrated calcein in the liposomes is released so that the concentration of calcein is reduced, causing fluorescence to be emitted. By measuring the fluorescent intensity, the activity of the antibody with respect to the antigen was determined.

Indirect ELISA was performed as follows. First, a solution of 100 ng/mL of PIP3 in 5 µg/mL of phosphatidylcholine (carrier) was charged in microtiter plates. It was allowed to stand overnight at room temperature for coating, then dried. The wells were then incubated in a blocking buffer (1% bovine serum albumin (BSA), 10 mM Hepes-buffered saline (HBS, pH 7.6)) for 30 minutes at room temperature. The blocked antigen-sensitized plates were washed, sealed and stored in a refrigerator until use.

After 100 µL each of PI-4,5-P2, IP3, IP4 and IP6 (serially diluted to $10^0$ to $10^4$ ng/mL with 0.5% BSA/HBS) and 100 µL of hybridoma supernatants were added to the wells of the antigen-sensitized plates, incubation was carried out at room temperature for 2 hours. The reaction solution was removed. After washing with HBS, a second antibody (alkaline phosphatase-labeled anti-mouse IgG3 or anti-mouse IgM; diluted to 1/2000 with 0.5% BSA/HBS) was added to the system followed by incubation at room temperature for 2 hours. After completion of the reaction, the unreacted antibodies were removed. The wells were again washed with HBS, and p-nitrophenyl phosphate (PNPP) was added to the wells to measure the activity of the alkaline phosphatase remaining in the wells. When the antibody contained in the culture supernatants was specific to PIP3, the immune reaction between the antibody and PIP3 proceeded without competitive inhibition by the various co-existing compounds. Thus, the higher alkaline phosphatase activity is retained in the solid phase. In contrast, when no antibody was contained in the culture supernatants or when the antibodies were cross-reactive with the various co-existing antigens, the number of antibodies that reacted with PIP3 on the solid phase was reduced due to competitive inhibition. As a result, the alkaline phosphatase activity retained on the solid phase became lower. The results of the culture supernatant of hybridoma AP3-11 obtained by ELISA are shown in FIG. 1. Since AP3-11 produces the antibody that reacts only with PIP3, a concentration-dependent decrease in binding percent (taking the absorbance obtained with the culture supernatant alone as 100%) is observed only for PIP3.

By this screening, two clones that produced an antibody reactive only with PIP3 and two clones that produce an antibody reactive with both PIP3 and PI-4,5-P2 were established. Designations of these clones are summarized in the table below. The antigen-bound activity of AP3-16 was calcium dependent. Among these clones, the reactivity was examined in more detail with the antibody produced by AP3-11 that was specific to PIP3 and non-cross-reactive with PI-4,5-P2 (hereinafter AP3-11 refers to the monoclonal antibody, unless otherwise indicated).

| Clone | Class | Specificity | Note |
|---|---|---|---|
| AP3-11 | IgG3 | PIP3 | |
| AP3-16 | IgM | PIP3 | $Ca^{2+}$ dependent |
| AP23-4 | IgG3 | PIP3/PI-4,5-P2 | |
| AP23-5 | IgG3 | PIP3/PI-4,5-P2 | |

EXAMPLE 2

Specificity of Anti-PIP3 Monoclonal Antibody AP3-11 (IgG3)

Among the antibodies obtained in Example 1, AP3-11 reacted only with PIP3 and showed the highest specificity to PIP3. The reactivity of this antibody was further analyzed by liposome lysis assay. Prior to the assay, pristane-treated mice were intraperitoneally inoculated with hybridoma AP3-11. Immunoglobulin was purified from the ascetic fluid by ammonium sulfate fractionation and used as monoclonal antibody AP3-11. The following lipid antigens were used for the liposome lysis assay.

phosphatidylcholine (PC)
phosphatidylserine (PS)
phosphatidic acid (PA)
phosphatidylinositol (PI)
cardiolipin (CL)
phosphatidylethanolamine (PE)

Figure 2:
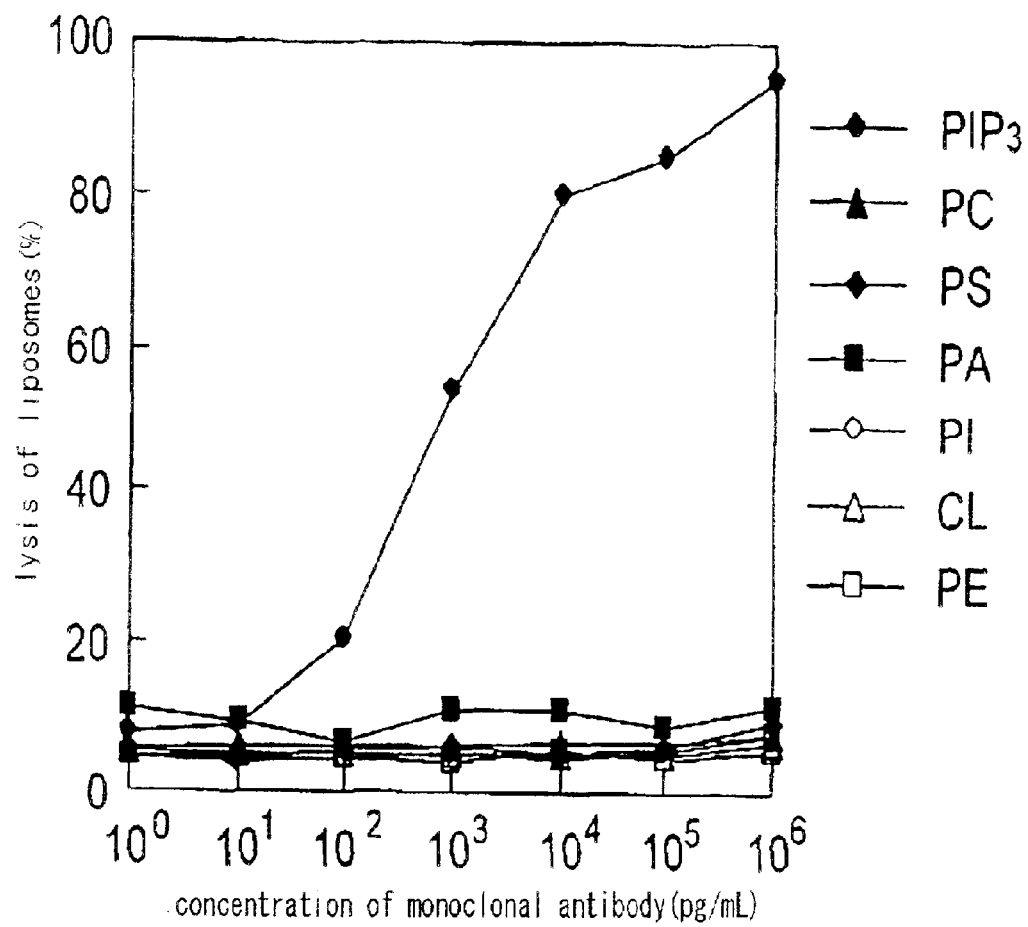
FIG. 2 shows graphs showing the results of liposome lysis assay performed to verify the binding activity of the antibody AP3-11 with various phospholipids. The ordinate designates the lysis (%) of liposomes, and the abscissa designates the concentration (pg/mL) of the antibody.

Liposomes prepared for the assay consisted of 50% cholesterol and 40% phosphatidylcholine as the main constituents and 10% of various different lipids as the remaining constituents. The liposomes different in composition were prepared in the same manner. The binding activity of AP3-11 was assayed by varying the antibody concentration in $100^0$ to $10^6$ pg/ML based on the liposomes. Lysis of the liposomes was observed to be concentration-dependent only in the liposomes containing PIP3 (PI-3,4,5-P3). In contrast, no lysis was observed in the liposomes containing other membrane-constructing phospholipids such as PC, PS, PA, PI, CL or PE, even when using the solution of the highest antibody concentration ($10^6$ pg/mL) prepared for the assay. The results are shown in FIG. 2. In FIG. 2, liposome lysis (%) refers to a percentage when the fluorescent intensity is made 100% when all of the liposomes reacted were lysed. The results reveal that AP3-11 reacted only with PIP3 in the phospholipids. To obtain more detailed information on an epitope recognized by AP3-11, the cross-reactivity of phosphatidylinositol with various phosphorylated antigen derivatives was examined.

Liposomes prepared for the assay consisted of 50% cholesterol, 40% phosphatidylcholine, and 9% dicetyl phosphate as the main constituents and 1% of the following phosphorylated phosphatidylinositol derivatives as the remaining constituents. In addition to this assay, direct ELISA was performed using microtiter plates to which PIP3 instead of the following compounds was immobilized.

PI-3,4,5-P3
PI-3,4-P2
PI-4,5-P2
PI

The assay was performed by varying the antibody concentration from $10^0$ to $10^6$ pg/mL. As in the previous experiment, lysis of the liposomes was observed to be concentration-dependent in the liposomes containing PIP3

Figure 3:
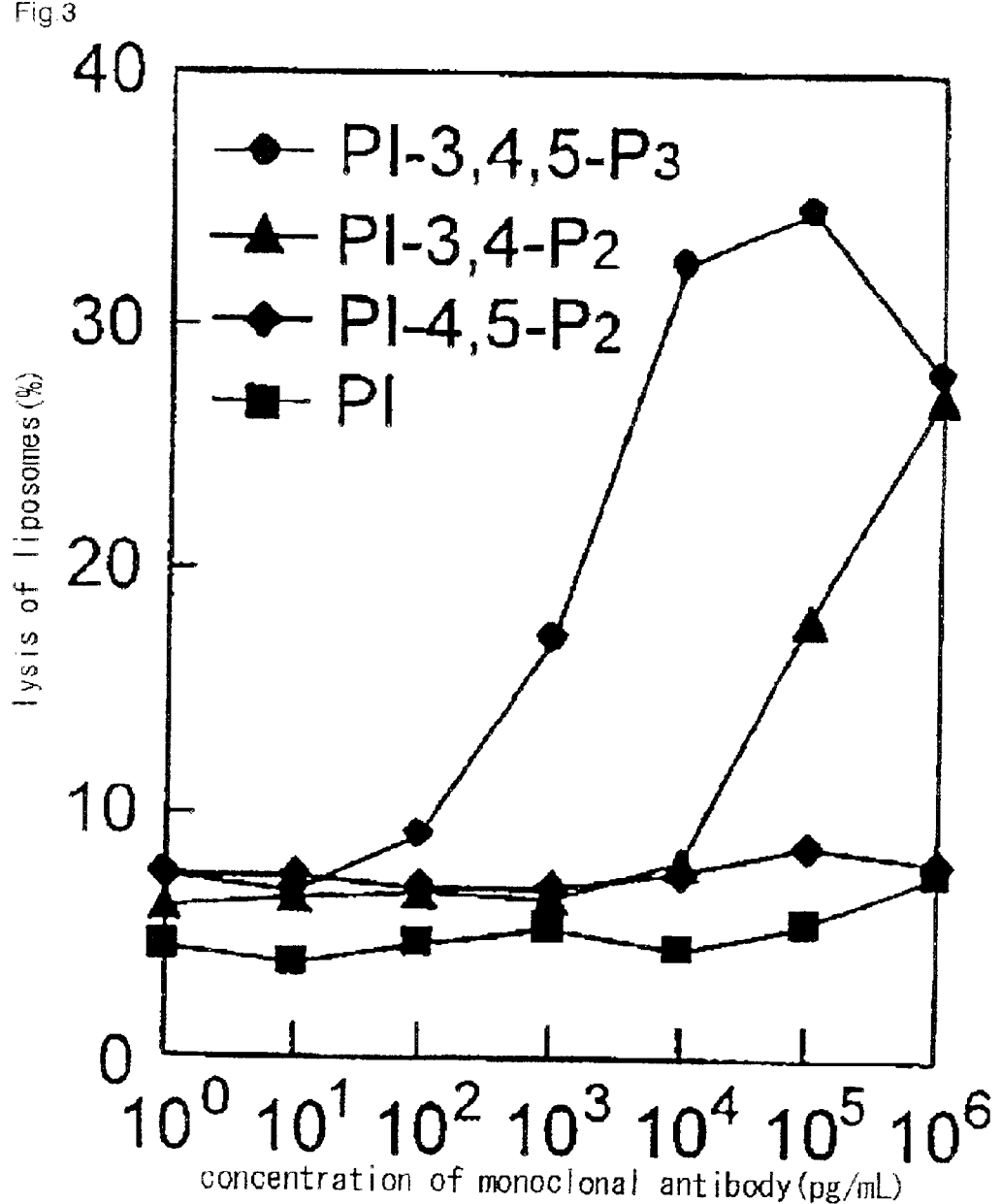
FIG. 3 shows graphs showing the results of liposome lysis assay performed to verify the binding activity of the antibody AP3-11 with various phosphatidylinositol polyphosphates. The ordinate designates the lysis (%) of liposomes, and the abscissa designates the concentration (pg/mL) of the antibody.
Figure 4:
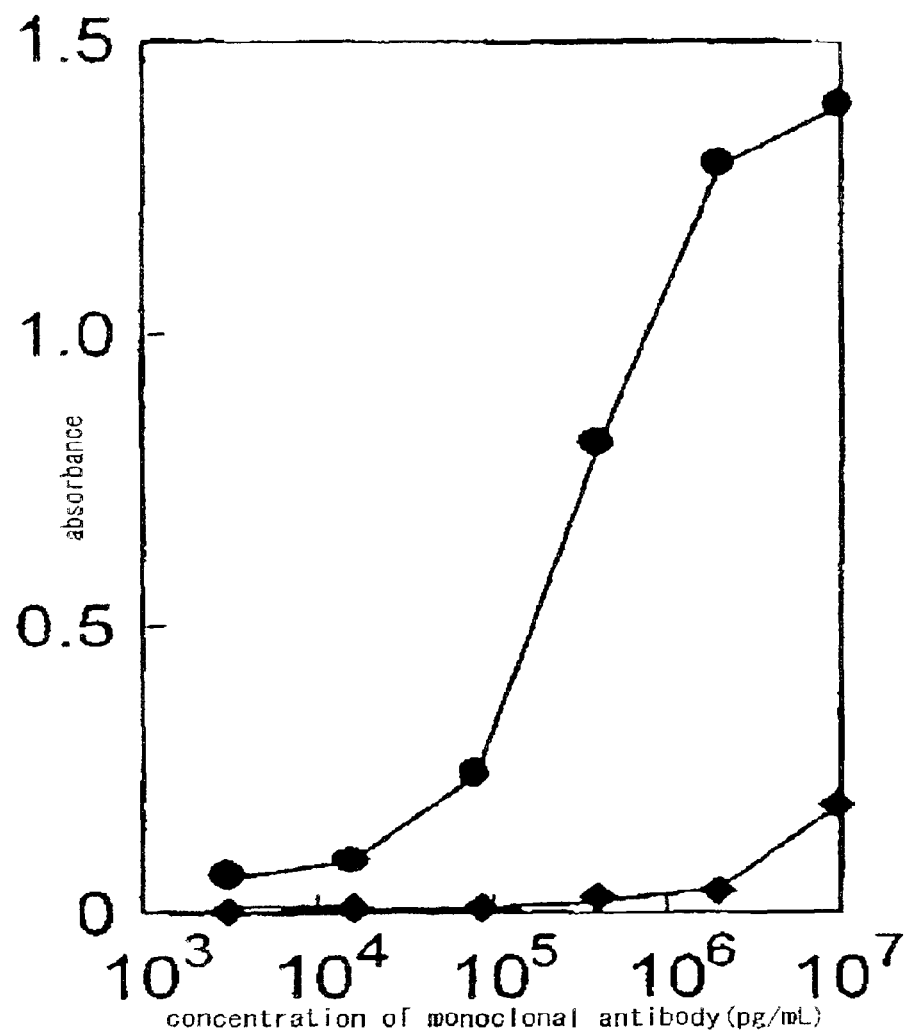
FIG. 4 shows graphs showing the results of ELISA performed to verify the binding activity of the antibody AP3-11 with PIP3 and PI-3,4-P2. The ordinate designates absorbance, and the abscissa designates the concentration (pg/mL) of the antibody.

(PI-3,4,5-P3). However, no reaction was observed in the liposomes containing PI or PI-4,5-P2, even when the solution of the highest antibody concentration ($10^6$ pg/mL) prepared for the assay was used. For PI-3,4-P2, a cross-reactivity of approximately 1/100 observed with PIP3 was noted. The results are shown in FIG. 3. Similar results were confirmed by direct ELISA as shown in FIG. 4. That is, the cross-reactivity of approximately 1/100 as compared to PIP3 was noted with PI-3,4-P2. The foregoing results reveal that the phosphate group at the 3-position of the inositol group plays the most important role for antigen recognition of AP3-11, and that the phosphate group at the 5-position also participates in the epitope configuration.

EXAMPLE 3

Epitope of Anti-PIP3 Monoclonal Antibody AP3-11 (IgG3)

To identify the recognition site of the AP3-11 antibody, indirect ELISA was performed using as competitors the following inositol polyphosphates ($10^0$ to $10^4$ nM) having a similar configuration to the inositol group of PIP3. The inositol polyphosphates used are given below.

inositol-1,4,5-triphosphate (IP3)

inositol-1,3,4,5-tetraphosphate (IP4)

inositol-1,2,3,4,5,6-hexaphosphate (IP6)

When free PIP3 was added as the competitor, absorbance was reduced in a concentration-dependent manner by competition with the fixed PIP3. Other inositol polyphosphates, such as IP3, IP4 and IP6, were not affected, as shown in FIG. 5.

These results suggest that the glycerol backbone is involved in the recognition site of the antibody. In order to verify whether the glycerol backbone constitutes the antibody recognition site, experiments were performed using PIP3 analogs fixed onto beads. The PIP3 analogs used are IP3-APB and PIP3-APB shown by the formulae below. As shown in the structural formulae, IP3-APB contains only the inositol structure of PIP3, and PIP3-APB contains both the inositol ring and a part of the glycerol backbone of PIP3.

IP3-APB

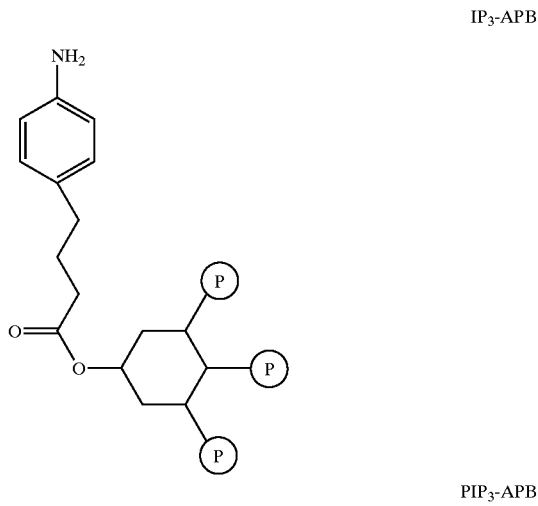

PIP3-APB

-continued

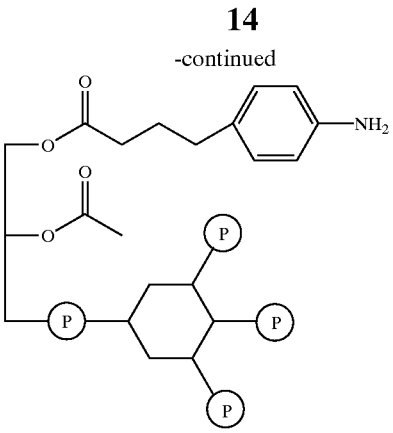

Figure 6:
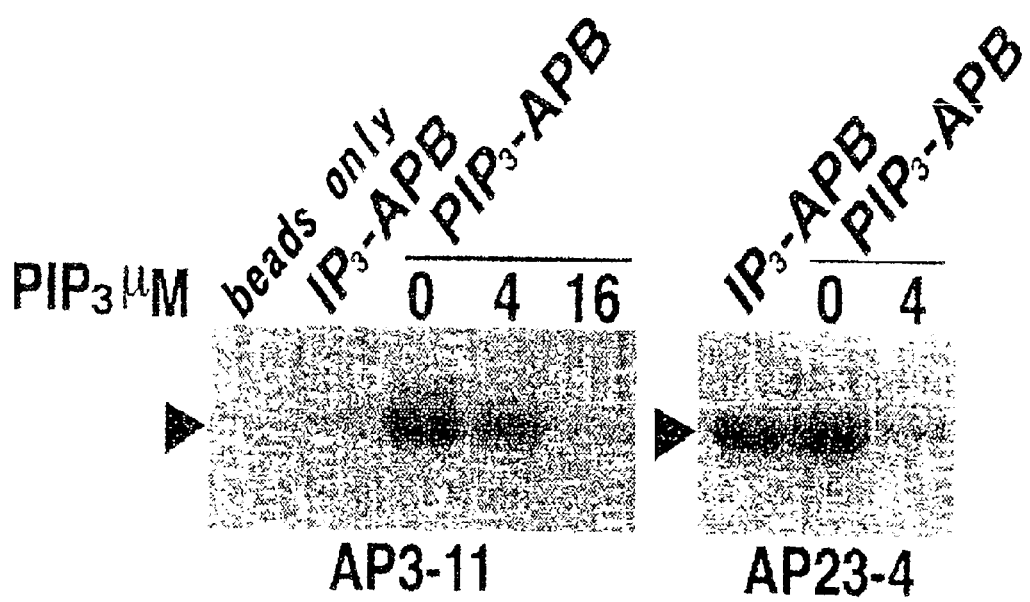
FIG. 6 shows photographs showing the results of CBB staining on SDS-PAGE indicating the binding activity of the antibody AP3-11 with various PIP3 analogs, in which the numerical figures designate the amount (μM) of PIP3 added for absorption of the antibody.
Figure 7:
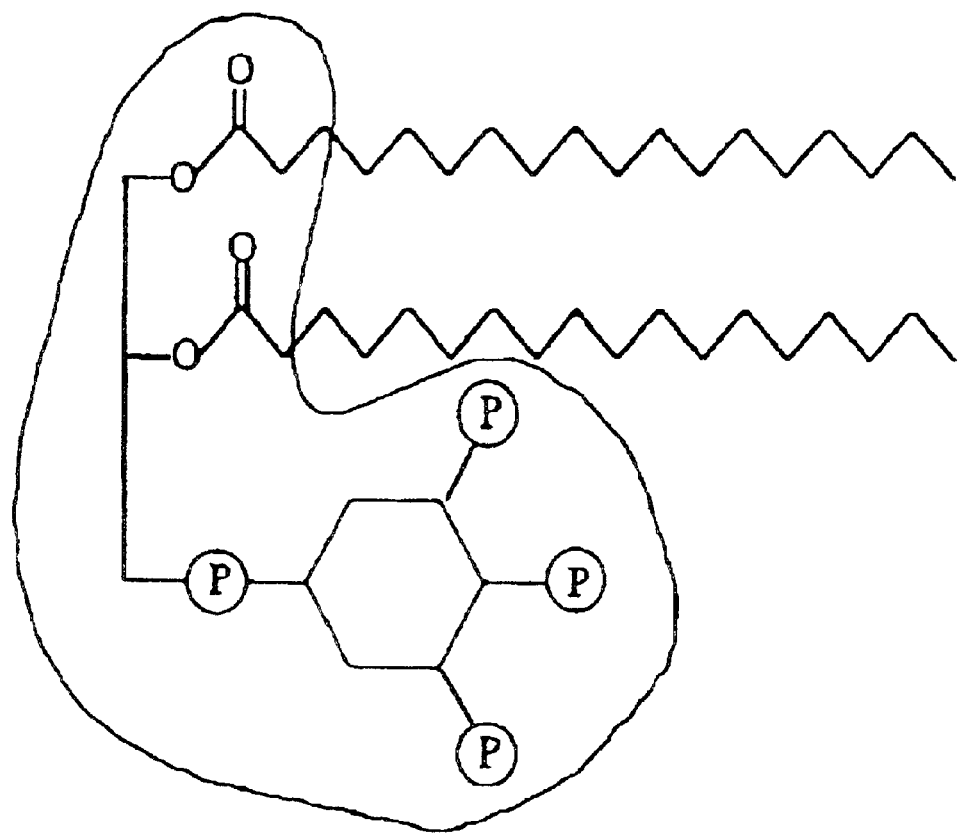
FIG. 7 schematically shows the epitope site of the antibody AP3-11.

Individual PIP3 analogs were fixed onto beads to react with AP3-11. After the beads were electrophoresed by SDS-PAGE, the beads were stained with CBB to detect the heavy chains of the antibody. AP3-11 bound to neither the beads themselves nor the IP3-APB-bound beads but bound to the PIP3-APB beads. When synthetic PIP3 was added as a competitor upon mixing the PIP3-APB beads and the antibody, the binding to the beads was inhibited, as shown in FIG. 6. These results indicate that AP3-11 recognizes as the epitope the portion shown in FIG. 7, containing the glycerol backbone of PIP3, and that the phosphate group at the 3-position of the inositol ring is extremely important.

The experimental results obtained with monoclonal antibody AP23-4 that reacted both with PIP3 and with PI-4,5-P2 are also shown in FIG. 6. AP23-4 was observed to bind to the IP3-APB beads. It is thus considered that AP23-4 recognizes the antigen only by its inositol ring.

Since the absorbance reduction depended on the concentration of PIP3 added, the antibody of the present invention makes the immunoassay possible, based on the competitive reaction of PIP3. Furthermore, the antibody of the present invention is not affected by various other compounds having similar configurations. Thus, the present invention can provide a simple assay system which is excellent in specificity to PIP3.

EXAMPLE 4

Identification of Hypervariable Regions (CDR) of Anti-PIP3 Monoclonal Antibody cDNA encoding the variable regions of the monoclonal antibody AP23-11 of the present invention that specifically recognizes PIP3 was cloned. RNA extracted from the hybridomas was subjected to RT-PCR for amplification of cDNA encoding the variable regions, using signal peptide and constant region sequences as primers. First, the hybridoma AP23-11 was incubated in DMEM/10% FCS to prepare poly $A^+$ RNA. Single-stranded cDNA was synthesized from 5 μg of the poly $A^+$ RNA. PCR was performed for 30 cycles, one cycle consisting of 94° C. for 1 minute, 55° C. for 2 minutes and 72° C. for 2 minutes. Restriction enzyme recognition sites corresponding to the cloning sites of pBluescript, which is a cloning vector, are provided at the 5' end of the primer used.

A band of about 400 bp was isolated from the amplification product by agarose gel electrophoresis and inserted into the cloning vector pBluescript. After the cloning, the vector was recovered. The nucleotide sequence of the insert was confirmed by the dideoxy method using the vector primer and [alpha-32] dATP (F. Sanger, Science, 214, 1205–1210, 1981).

The amino acid sequence for the thus obtained gene encodes was deduced, and hypervariable regions CDR were identified by the Chothia Numbering Scheme Al-Lazikani et al., J. Molec. Biol., 273, 927–948, 1997). The amino acid sequences constructing the thus identified variable regions of the heavy chains, light chains, and CDRs are shown in FIG. 8. The amino acid residues marked with the arrow in FIG. 8 hardly appear at these positions in conventional antibodies, according to the antibody database. The amino acid residues located in the CDRs thus seem to participate in the specificity. In order to obtain mutants of the amino acid sequences, the sequence containing the amino acid residues should be selected.

What is claimed is:

1. An immunoassay method comprising the steps of:
   (a) reacting a monoclonal antibody specifically recognizing phosphatidylinositol-3,4,5-triphosphate, or a variable region thereof, with phosphatidylinositol-3,4,5-triphosphate present in a sample; and,
   (b) detecting the binding based on an immunological reaction between said antibody, or said variable region thereof, and said phosphatidylinositol-3,4,5-triphosphate; wherein, said monoclonal antibody binds to an antigenic determinant that contains an inositol group and a glycerol backbone in said phosphatidylinositol-3,4,5-triphosphate.

2. The immunoassay method of claim 1, wherein said monoclonal antibody does not cross-react with phosphatidylinositol-4,5-biphosphate.

3. An immunoassay method which comprises the steps of:
   (a) reacting a monoclonal antibody specifically recognizing phosphatidylinositol-3,4,5-triphosphate, or a variable region thereof, with phosphatidylinositol-3,4,5-triphosphate present in a sample; and,
   (b) detecting the binding based on an immunological reaction between said antibody, or said variable region, thereof, and the phosphatidylinositol-3,4,5-triphosphate; wherein, said monoclonal antibody is an immunoglobulin, or a variable region thereof, which recognizes the phosphatidylinositol-3,4,5-triphosphate; wherein, said immunoglobulin, or said variable region thereof, comprises an immunoglobulin heavy chain comprising:
   (i) CDR1 comprising the amino acid sequence of SEQ ID NO: 5;
   (ii) CDR2 comprising the amino acid sequence of SEQ ID NO: 6; and,
   (iii) CDR3 comprising the amino acid sequence of SEQ II) NO: 7.

4. The immunoassay method according to claim 3, wherein said immunoglobulin comprises an immunoglobulin light chain comprising:
   (i) CDR1 comprising the amino acid sequence of SEQ ID NO: 8;
   (ii) CDR2 comprising the amino acid sequence of SEQ ID NO: 9; and,
   (iii) CDR3 comprising the amino acid sequence of SEQ ID NO: 10.

* * * * *

UNITED STATES PATENT AND TRADEMARK OFFICE
CERTIFICATE OF CORRECTION

PATENT NO. : 6,818,408 B2
DATED : November 16, 2004
INVENTOR(S) : Y. Fukui et al.

It is certified that error appears in the above-identified patent and that said Letters Patent is hereby corrected as shown below:

Title page,
Item [75], Inventors, please correct "Ryuichi Shirai, Yokohama (JP)" to -- Ryuichi Shirai, Kanagawa (JP) --.
Item [56], References Cited, OTHER PUBLICATIONS, "Van der Kaay" reference, please correct "Triphosphate" to -- Trisphosphate --; "Fry" reference, please correct "1225" to -- 1226 --.

Column 8,
Line 6, please correct "(ScFV)" to -- (scFV) --.

Column 12,
Line 36, please correct "100°" to -- 10° --.

Column 16,
Line 7, please correct "region," to -- region --.
Line 20, please correct "II) NO: 7." to -- ID NO: 7. --.

Signed and Sealed this

Thirtieth Day of August, 2005

JON W. DUDAS
*Director of the United States Patent and Trademark Office*